United States Patent [19]

Sprecker et al.

[11] 4,205,186

[45] * May 27, 1980

[54] PROCESS FOR PREPARING SUBSTITUTED OXYACETALDEHYDES AND ACETALS THEREOF

[75] Inventors: Mark A. Sprecker, Sea Bright; John J. Kryschuk, Howell; John B. Hall, Rumson, all of N.J.

[73] Assignee: International Flavors & Fragrances Inc., New York, N.Y.

[*] Notice: The portion of the term of this patent subsequent to Nov. 7, 1995, has been disclaimed.

[21] Appl. No.: 3,883

[22] Filed: Jan. 16, 1979

Related U.S. Application Data

[60] Continuation-in-part of Ser. No. 928,717, Jul. 27, 1978, abandoned, which is a division of Ser. No. 811,480, Jun. 30, 1977, abandoned.

[51] Int. Cl.² ............................................. C07C 43/30
[52] U.S. Cl. ................................... 568/600; 568/496; 568/483; 568/486
[58] Field of Search ........................................ 568/600

[56] References Cited

U.S. PATENT DOCUMENTS

| | | | |
|---|---|---|---|
| 2,186,630 | 1/1940 | Dickey et al. | 568/600 |
| 2,409,015 | 10/1946 | Bordenca et al. | 568/600 |
| 3,931,238 | 1/1976 | Starks | 568/600 |

OTHER PUBLICATIONS

Freedman et al., Tetrahedron Letters, No. 38, pp. 3251–3254, 1975.
Starks, II, J.A.C.S., vol. 43, pp. 195–199, 1971.

*Primary Examiner*—Howard I. Mars
*Attorney, Agent, or Firm*—Arthur L. Liberman; Franklin D. Wolffe

[57] ABSTRACT

A process is described for the preparation of substituted oxyacetaldehydes and acetals thereof according to the reaction sequence:

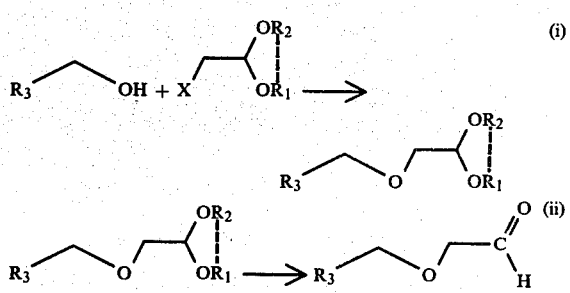

wherein $R_1$ and $R_2$ are each lower alkyl or $R_1$ and $R_2$, taken together form a lower alkylene group; wherein $R_3$ is alkyl, alkenyl or alkadienyl and X is halogen selected from the group consisting of chlorine and bromine, the reaction (i) being carried out (1) using a "phase transfer agent" and (2) in a two phase system.

2 Claims, 15 Drawing Figures

IR SPECTRUM FOR EXAMPLE I

GLC PROFILE FOR EXAMPLE II, REACTION PRODUCT

I R SPECTRUM FOR EXAMPLE III

GLC PROFILE FOR EXAMPLE III, REACTION PRODUCT

FIG.10 — IR SPECTRUM FOR EXAMPLE II

FIG.12 IR SPECTRUM FOR EXAMPLE III

GLC PROFILE FOR EXAMPLE IV

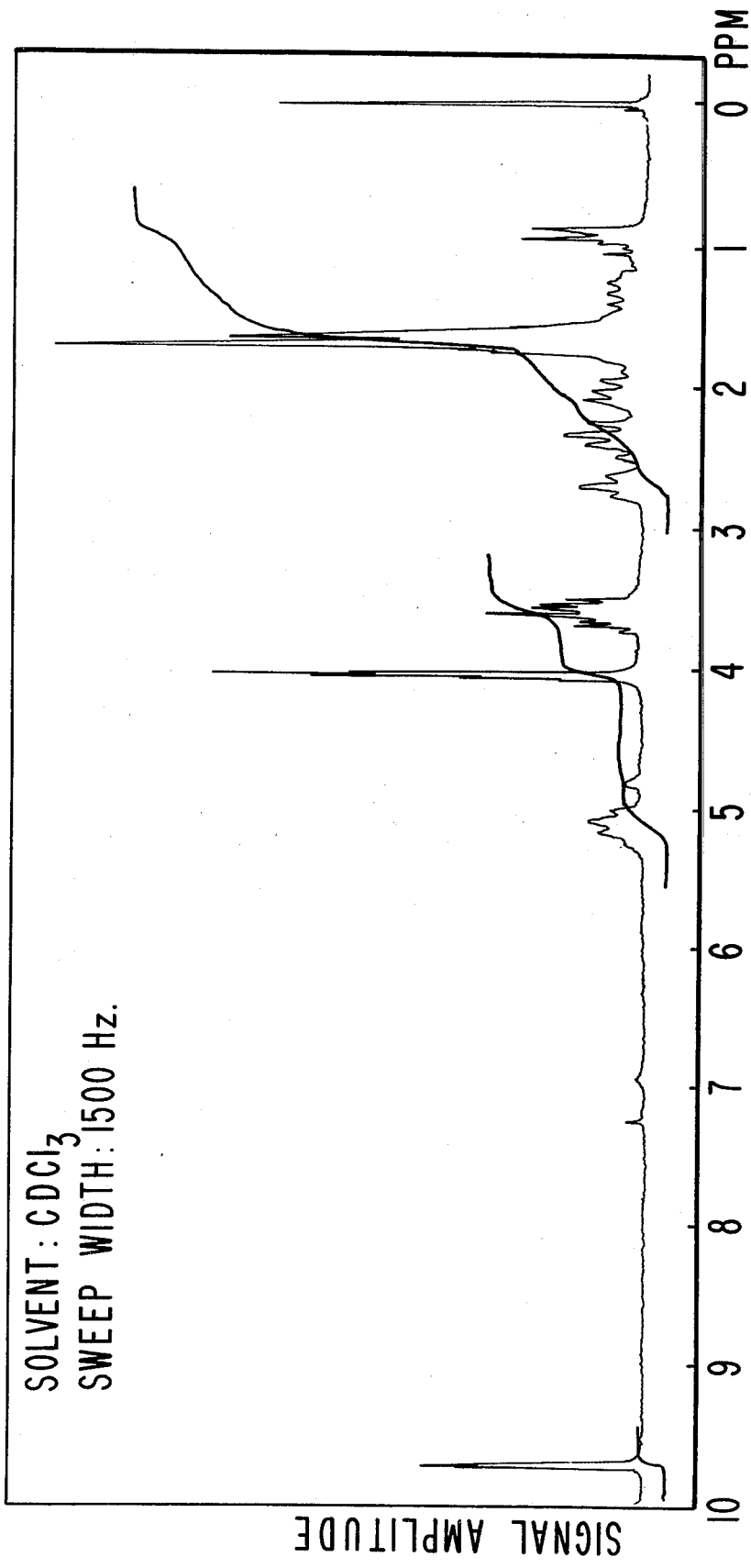

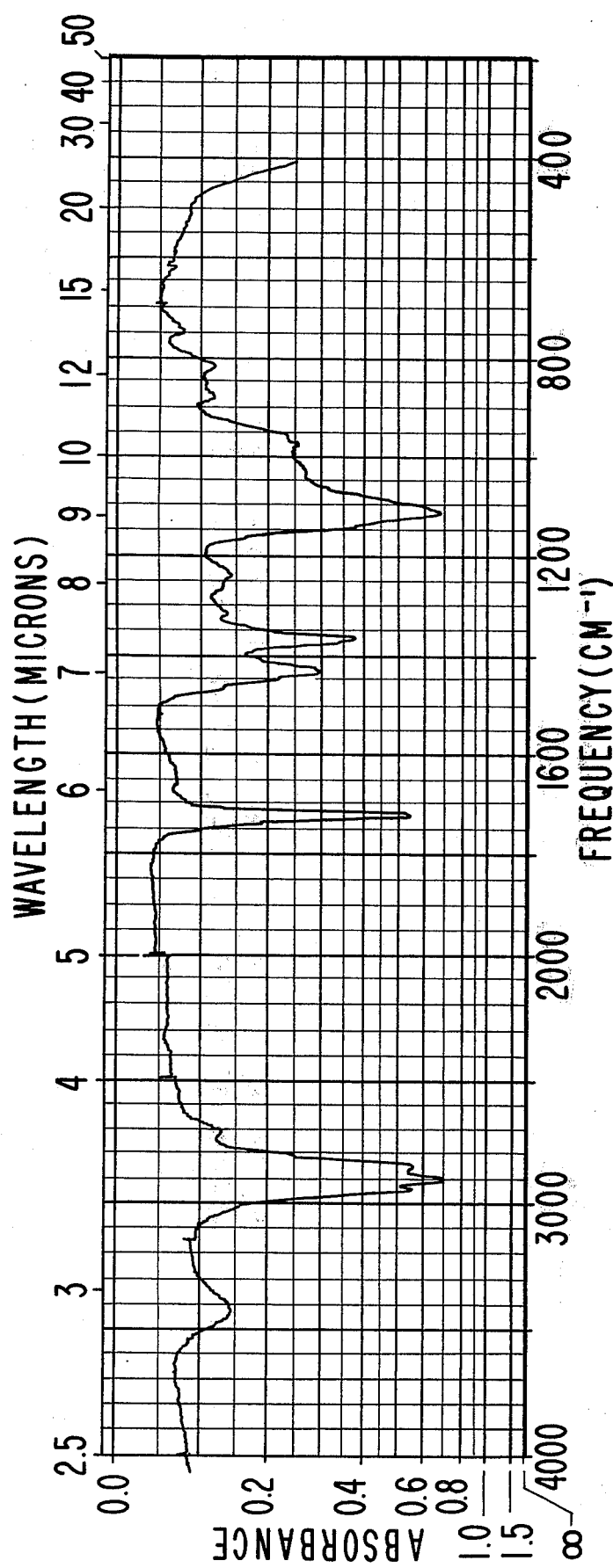

PROCESS FOR PREPARING SUBSTITUTED OXYACETALDEHYDES AND ACETALS THEREOF

This application is a continuation in part of Application for United States Letters Patent, Ser. No. 928,717 filed on July 27, 1978, now abandoned, which, in turn, is a division of Application for United States Letters Patent, Ser. No. 811,480 filed on June 30, 1977, now abandoned.

BACKGROUND OF THE INVENTION

This invention provides processes for preparing certain valuable substances useful in the formation of perfume materials. More specifically, this invention provides a process for preparing substituted oxyacetaldehydes and acetals thereof. The substituted oxyacetaldehydes have the formula:

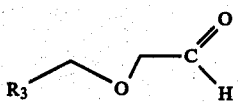

and the substituted oxyacetaldehyde acetals have the formula:

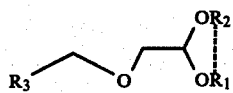

wherein $R_1$ and $R_2$, taken separately are each the same or different lower alkyl or $R_1$ and $R_2$, taken together, represent a lower alkylene moiety; and where $R_3$ is alkyl, alkenyl and alkadienyl.

Examples of the compounds prepared according to the process of this invention are the aldehydes, citronellyl oxyacetaldehyde, geranyl oxyacetaldehyde and n-octyl oxyacetaldehyde. Corresponding methyl and ethyl acetals are also examples of the compounds prepared according to the process of the instant invention.

Citronellyl oxyacetaldehyde, having the structure:

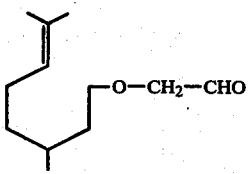

is described by Arctander, "Perfume and Flavor Chemicals" (Aroma Chemicals), Vol. I, 1969, #688. This aldehyde is described as having a "powerful and moderately diffusive green-rosey, sweet Lily-Muguet-like odor". As stated by Arctander, citronellyl oxyacetaldehyde is:

"Used in perfume compositions as a floralizing aldehydic topnote ingredient, primarily in Muguet-Lily fragrances, but also in Rose Peony (where the Geranyl-isomer is claimed to be superior), and various modifications of modern-aldehydic fragrance types.

Occasionally used in flavor compositions for floral or fruity types, and in Rose type flavors. The concentration is usually mere traces in the finished product."

Arctander states that this material is produced from Citronellol, which is first reacted with sodium methylate or sodium iso-propylate. The thus formed sodium citronellol organometallic compound is then reacted with chlorodimethylacetal to produce the citronellyl oxyacetaldehyde dimethylacetal. The thus formed citronellyl oxyacetaldehyde dimethylacetal is finally hydrolyzed with dilute oxalic acid to yield the desired aldehyde, the citronellyl oxyacetaldehyde.

In monograph 689 of Arctander, "Perfume and Flavor Chemicals" (Aroma Chemicals), Vol. I, 1969, Arctander describes citronellyl oxyacetaldehyde diethylacetal having the formula:

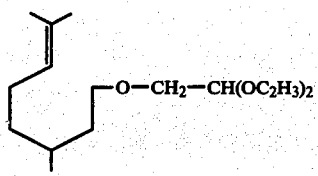

This compound is described as having a "very faint, delicate, Rose-Muguet-type odor". It is also stated to be somewhat more oily and more tenacious than the aldehyde, but much weaker.

Bedoukian, "Perfumery and Flavoring Synthetics", Elsevier Publishing Co., 2nd Revised Edition, 1967, describes at page 378 in the section entitled: "The Oxy-Acetaldehydes" various oxyacetaldehydes for use in perfumery, e.g., citronellyl oxyacetaldehyde, geranyl oxyacetaldehyde, phenylethyl oxyacetaldehyde, benzyl oxyacetaldehyde and decyl oxyacetaldehyde and the corresponding acetals. Bedoukian reports that various references describe the preparation of these oxyacetaldehydes and their acetals by interaction of "bromo acetals with sodium or potassium alcoholates". Thus, Bedoukian states:

"In 1872, Pinner (Ber. 5 (1872) 159) reported the preparation of a number of oxy-acetaldehydes and their acetals by the interaction of bromoacetals with sodium or potassium alcoholates. It was not until 1929, however, that the value of these compounds as perfumery materials was brought to the attention of the industry by Sabetay and co-workers (Bull. Soc. Chim. France, 45 (1929) 1161 and Compt. Rend., 194 (1932) 617 and 196 (1933) 1508). Further work on the preparation of this class of compounds was done by Rothard (Compt. Rend., 196 (1933) 2013; 197 (1933) 1225) and Shoruigin and Korshak (Ber., 68B (1935) 838 and Chem. Abstracts, 29 (1935) 7941), who reported the odor characteristics of many of these compounds."

Neither the references cited by Bedoukian nor the references cited by Arctander disclose the one-step or two-step efficient process of the instant invention (depending on whether acetals or aldehydes are desired to be produced).

In performing the one-step or two-step process of the instant invention, quaternary ammonium salts are used as catalysts or reaction "promoters". Thus, whereas the instant invention discloses and claims the reaction sequence:

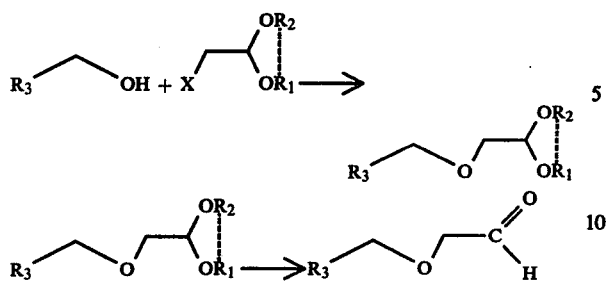

the prior art, as embodied in Bedoukian and Arctander, discloses the three-step reaction sequence, illustrated thusly:

Arctander and Bedoukian Process Disclosed by:

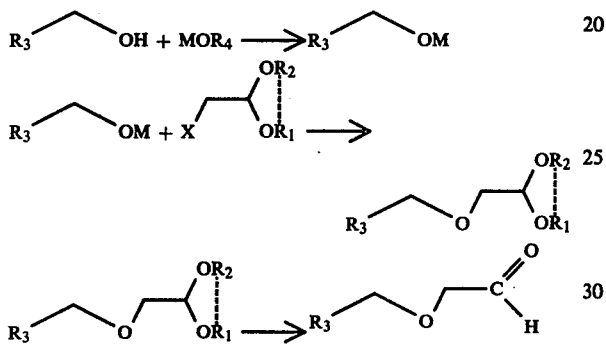

wherein $R_3$ is alkyl, alkenyl or alkadienyl; wherein $R_4$ is lower alkyl; wherein M is potassium or sodium; wherein X is chlorine or bromine and wherein $R_1$ or $R_2$ are lower alkyl or represent an alkylene moiety.

Production of mixed ethers from alkyl halides and alkanols are disclosed using quaternary ammonium salts in the Eastman Organic Chemicals Bulletin, Vol. 48, #1, 1976, page 2, section entitled: "Unsymmetrical Ethers". In addition, the Eastman Organic Chemicals Bulletin discloses the production of aryl alkyl ethers using quaternary ammonium salts. Nevertheless, the production of the alkyl, alkenyl and alkadienyl oxyacetaldehydes and oxyacetaldehyde acetals is not disclosed, either implicitly or explicitly, by either the Eastman Organic Chemicals Bulletin or any of the other prior art where quaternary ammonium salts are used as reaction promoters. Also relevant is the article, Freedman and Dubois, Tetrahedron Letters, No. 38, pages 3251–3254, 1975, "An Improved Williamson Ether Synthesis Using Phase Transfer Catalysis".

THE INVENTION

The invention accordingly comprises the novel process and step or steps, specific embodiments of which are also described hereinafter by use of experiments and in accordance with what is now the preferred practice of the invention.

The process of our invention comprises reacting a primary alcohol having the structure:

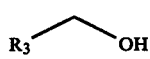

with a halo acetaldehyde acetal having the structure:

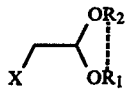

wherein X is chloro or bromo and $R_1$ and $R_2$, taken separately, are the same or different and represent lower alkyl, or taken together, represent lower alkylene, to form a substituted oxyacetaldehyde acetal having the structure:

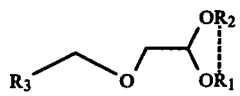

This substituted oxyacetaldehyde acetal may be used "as is" or if desired, it may then be hydrolyzed to form the substituted oxyacetaldehyde having the structure:

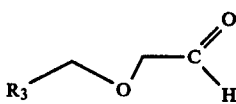

The first reaction to form the ether-acetal takes place in the presence of alkali metal hydroxides and one or more "phase transfer agents". The reaction is carried out in a two-phase system in the absence of a solvent or the presence of an inert solvent.

More specifically, the first step of our invention provides a process for the etherification of alkanols, alkenols and alkadienols with halogenated acetaldehyde acetals under the influence of a base comprising the step of placing the reactants for the process and the base respectively in two immiscible phases; an organic phase and a solid base phase with the reactants being located substantially entirely in the first mentioned organic phase and the base being located substantially entirely in the second mentioned phase; and adding to the two phase system a "phase transfer agent" which may be one or more of several organic quaternary ammonium salts.

Specific examples of "phase transfer agents" useful in our invention are as follows:

Tricapryl methyl ammonium chloride;
Cetyl trimethyl ammonium bromide; and
Benzyl trimethyl ammonium hydroxide.

In general, the "phase transfer agents" most preferred have the generic formula:

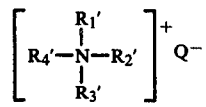

wherein at least one of $R_1'$, $R_2'$, $R_3'$ and $R_4'$ is $C_6$-$C_{14}$ aryl, $C_6$-$C_{10}$ alkaryl, $C_6$-$C_{20}$ alkyl, $C_6$-$C_{14}$ aralkyl and $C_6$-$C_{20}$ alkenyl and the other of $R_2'$, $R_3'$ and $R_4'$ is alkyl such as methyl, ethyl, n-propyl, i-propyl, 1-butyl, 2-butyl, 1-methyl-2-propyl, 1-pentyl and 1-octyl and $Q^-$ is an anion such as chloride, bromide and hydroxide.

The process of our invention is carried out at a temperature in the range of from about 120° C. up to about 200° C. with a temperature range of about 135°–145° C. being preferred. The reaction time is inversely proportional to the reaction temperature, with lower reaction temperatures giving rise to greater reaction times; and, accordingly, the reaction time ranges from about 5 hours up to 14 hours. It is noteworthy that excessive reaction times are not preferred due to the formation of a side product which is a trialkoxy ethane having the generic structure:

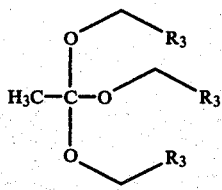

In the reaction of our invention the mole ratio of hydroxy compound (having the formula:

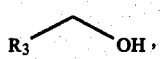

to halo acetaldehyde (having the structure:

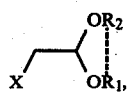

is preferably about 1:1, but may vary between 0.5:1 to 2:1. In the reaction of our invention the mole ratio of said hydroxy compound to base is preferably about 1:1.5, but may vary between 1:1 and 1:2. In any event, it is preferable to use an excess of base with respect to hydroxyl compound having the structure:

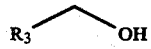

The quantity of "phase transfer agent" in the reaction mass based on amount of halogenated acetaldehyde acetal in the reaction mass may vary from 0.5 grams per mole of halogenated acetaldehyde acetal up to 25 grams of "phase transfer agent" per mole of halogenated acetaldehyde acetal, with a preferred concentration of "phase transfer agent" being in the range of from about 2.5 up to about 7.5 grams of "phase transfer agent" per mole of halogenated acetaldehyde acetal.

The reaction of our invention is preferably carried out at atmospheric pressure since that is the most convenient condition. However, lower or higher pressures can be used without detrimentally affecting the ultimate yield of desired product.

In the single step etherification reaction, bases used in said reaction are sodium hydroxide and potassium hydroxide.

Certain bases will not give rise to any reaction, e.g., lithium hydroxide, calcium hydroxide or barium hydroxide.

The etherification reaction of the process of our invention is preferably best carried out in the absence of solvent; however, solvents such as xylene or higher boiling hydrocarbons, e.g., decalin can be used, but use of such solvents slows down the rate of reaction. In any event, alcohols and halogenated chlorocarbon solvents such as dichlorobenzene should not be used as a reaction solvent. Furthermore, toluene and benzene should not be used as the etherification reaction solvent, since the temperature of reaction must be above 120° C. and the use of such solvents at atmospheric pressure, in particular, will cause the reaction not to take place.

The resulting substituted oxyacetaldehyde acetals may be use in perfumery or in perfumed articles as such or they may be, if desired, hydrolyzed to their corresponding aldehydes. The hydrolysis step of the reaction sequence of our invention may be carried out under standard conditions with the exception that care must be taken that when the acetal moiety is hydrolyzed, the ether linkage is not cleared. Accordingly, the particular hydrolysis reagents used for hydrolyzing the acetal are critical. Thus, for example, oxalic acid, dilute aqueous hydrochloric acid, dilute aqueous sulfuric acid or aqueous formic acid, may be used to hydrolyze the acetal to the corresponding aldehydes.

As a general rule, the preferable reactions of our invention are illustrated by the following reaction sequence:

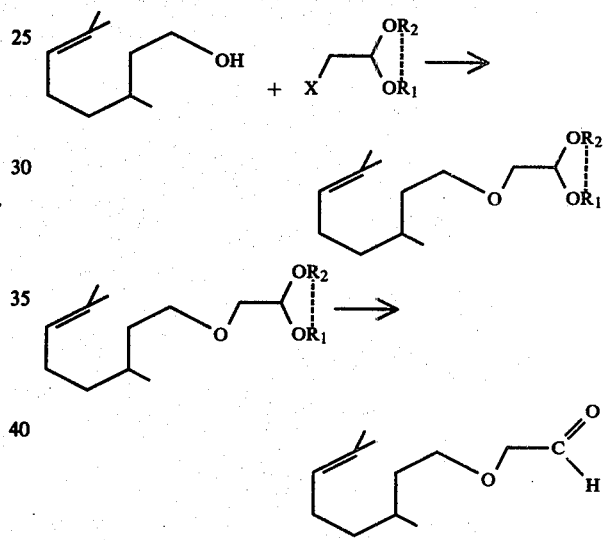

wherein X is chloro or bromo, $R_1$ and $R_2$ are each, taken separately, the same or different lower alkyl or $R_1$ and $R_2$, taken together form a lower alkylene moiety. More specifically, the reactions of our invention are illustrated most preferably by the following reaction sequences:

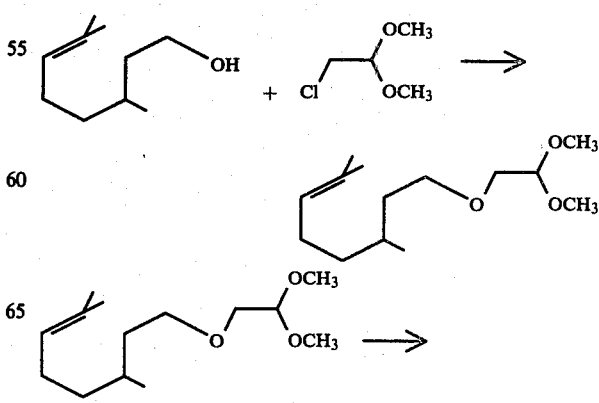

-continued

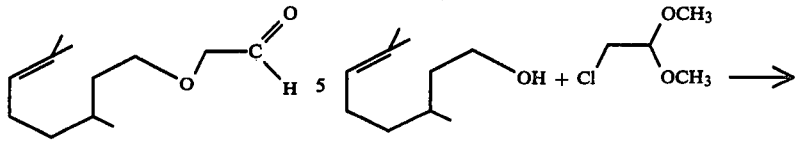

(production of citronellyl oxyacetaldehyde dimethyl acetal followed by production of citronellyl oxyacetaldehyde);

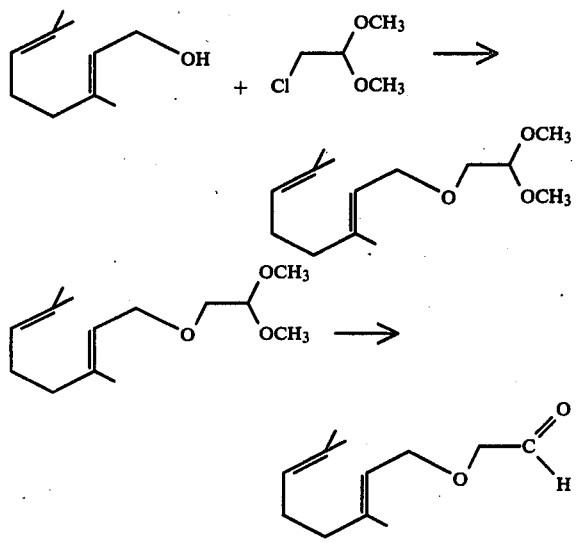

(production of geranyl oxyacetaldehyde dimethyl acetal followed by production of geranyl oxyacetaldhyde); and

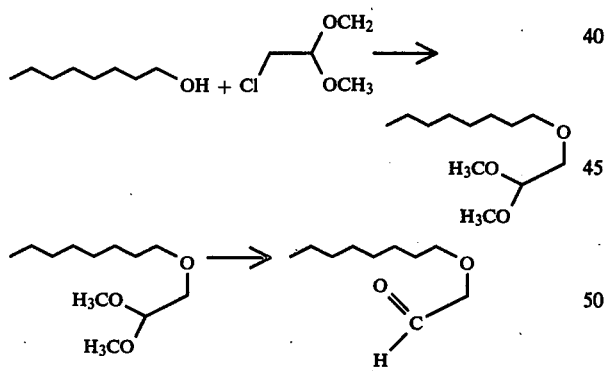

(production of octyl oxyacetaldehyde dimethyl acetal followed by production of octyl oxyacetaldehyde).

The following Examples I, II and III serve to illustrate embodiments of our invention as it is now preferred to practice it. Example IV illustrates the utility of one of the compounds produced according to the process of our invention. It will be understood that these Examples are illustrative and restricted thereto only as defined in the appended claims.

EXAMPLE I

Preparation of Citronellyl Oxyacetaldehyde Dimethyl Acetal

Reaction:

A mixture of 3050 grams of citronellol (containing approximately 10% of 3,7-dimethyl octanol), 1200 grams of granular sodium hydroxide and 95 grams of Aliquat 336 ® (registered trademark of General Mills Chemicals, Inc., identifying tricapryl methyl ammonium chloride) is heated to 140° C. with vigorous stirring. 2492 Grams of chloroacetaldehyde are then added over a 30 minute period and the mixture is heated at reflux for a period of 7 hours. 5 Liters of water is added to the cooled reaction mass and stirring is continued until all solids are dissolved. The aqueous phase is discarded and 300 ml of toluene, 75 grams of Primol ® and 0.2 grams of Ionox ® are added to the organic phase. Distillation affords 2142 grams of recovered citronellol (boiling point 88° C. at 5 mm Hg pressure) and 2380 grams of citronellyl oxyacetaldehyde dimethyl acetal (boiling point 109°–112° C.; 2.9 mm Hg pressure containing about 10% of 3,7-dimethyloctyloxyacetaldehyde dimethyl acetal) resulting in a 39% conversion (86% yield), based on starting alcohol.

FIG. 1 is the NMR spectrum for citronellyl oxyacetaldehyde. FIG. 2 is the infrared spectrum for citronellyl oxyacetaldehyde. (In both spectra, approximately 10% of the dimethyl octanol derivatives are present).

EXAMPLE II

Preparation of n-Octyl Oxyacetaldehyde Dimethyl Acetal

Reaction:

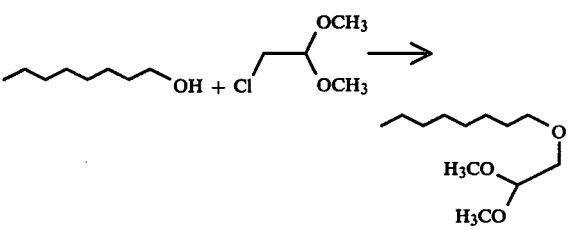

A mixture of 130 grams of n-octanol, 60 grams of granular sodium hydroxide, 4 grams of Aliquat 336 ® (registered trademark of General Mills Chemicals, Inc.) and 110 grams of chloro acetaldehyde dimethyl acetal are heated to reflux for 4 hours. The reaction mass is cooled and 200 ml of water are added thereto with vigorous stirring. After all solids are dissolved, the aqueous phase is distilled to yield 87 grams of n-octanol (boiling point 60° C. at 1.4 mm Hg pressure) and 77 grams of n-octyl oxyacetaldehyde (boiling point 90° C. at 1.8 mm Hg). The conversion based on chloroacetaldehyde dimethyl acetal is 40% and the yield based on n-octanol is 83%.

The GLC profile for the reaction mass produced as indicated above is set forth in FIG. 3. The NMR spectrum for octyl oxyacetaldehyde dimethyl acetal is set forth in FIG. 4. The infrared spectrum for octyl oxyacetaldehyde dimethyl acetal is set forth in FIG. 5.

EXAMPLE III

Preparation of Geranyl/Neryl Oxyacetaldehyde Dimethyl Acetal

Reaction:

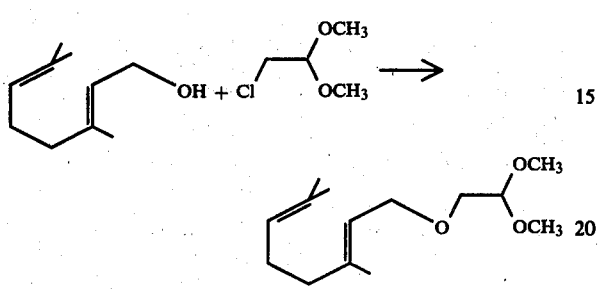

A mixture of 770 grams of "INTERMEDIATE GERANIOL 60" sold by the Glidden Corporation of Jacksonville, Florida (a mixture of geraniol and nerol, containing 60 weight percent geraniol and 40 weight percent nerol), 311 grams of chloroacetaldehyde dimethyl acetal, 150 grams of granular sodium hydroxide and 25 grams of Aliquat 336 ® (registered trademark of General Mills Chemicals, Inc.) is heated at reflux for 13 hours. The reaction mass is cooled to room temperature and 500 ml of water are added with vigorous stirring. The organic phase is distilled through a 1"×12" Goodloe packed column using a reflux ratio of 4:1 after adding to the reaction mass 50 grams of toluene, 10 grams of Primol ® and 0.1 grams of Ionox ®, affording 441 grams of geranyl/neryl oxyacetaldehyde dimethyl acetal (boiling point 17° C. at 2.5 mm Hg pressure). The conversion to product based on chloroacetaldehyde dimethyl acetal is 36% and the yield based on unrecovered geraniol is 43%.

The mass spectral data for the geranyl/neryl oxyacetaldehyde dimethyl acetal is as follows:

m/e=75, 41, 69, 43, 39

FIG. 6 is the NMR spectrum for the mixture of geranyl oxyacetaldehyde dimethyl acetal and neryl oxyacetaldehyde dimethyl acetal produced as indicated above. FIG. 7 is the infrared spectrum for the mixture of geranyl oxyacetaldehyde dimethyl acetal and neryl oxyacetaldehyde dimethyl acetal produced as indicated above. FIG. 8 is the GLC profile for the reaction product containing the mixture of neryl oxyacetaldehyde dimethyl acetal and geranyl oxyacetaldehyde dimethyl acetal produced as indicated above.

The mixture of geranyl oxyacetaldehyde dimethyl acetal and neryl oxyacetaldehyde dimethyl acetal is separated using preparative GLC (conditions: 10% SE-30 column, 10′×¼″, isothermal operated at 220° C.). The geranyl oxyacetaldehyde dimethyl acetal is thus separated from the neryl oxyacetaldehyde dimethyl acetal. FIG. 9 is the NMR spectrum for geranyl oxyacetaldehyde dimethyl acetal produced as indicated above. FIG. 10 is the infrared spectrum for geranyl oxyacetaldehyde dimethyl acetal produced as indicated above. FIG. 11 is the NMR spectrum for neryl oxyacetaldehyde dimethyl acetal produced as indicated above. FIG. 12 is the infrared spectrum for neryl oxyacetaldehyde dimethyl acetal produced as indicated above.

EXAMPLE IV

Preparation of Geranyl Oxyacetaldehyde

Reaction:

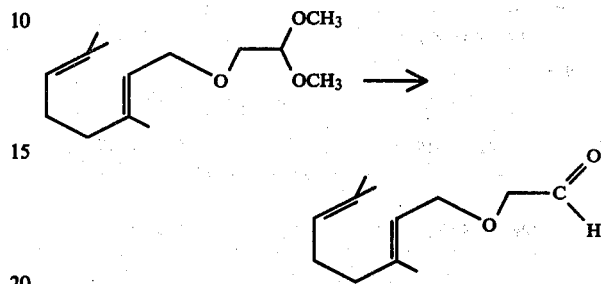

Into a 1 liter reaction flask equipped with thermometer, stirrer, heating mantle and reflux condenser is placed the following materials:

| | |
|---|---|
| Geranyl oxyacetaldehyde dimethyl acetal | 378 grams |
| Formic acid | 300 grams |
| Water | 900 grams |

The reaction mass is heated to 80° C. for a period of 6 hours with GLC samples (200° C. isothermal SE-30 column) taken every 90 minutes. At the end of the 6 hour period, 1.33 liters of water is added to the reaction mass. Sodium bicarbonate is added to the organic phase to a pH of 7. 200 ml benzene is then added to the organic phase. 10 Grams of Primol ® is also added and the resulting material is distilled yielding 120 grams of geranyl oxyacetaldehyde (boiling point 115°-121° C. at 3 mm Hg). The reaction product, at the end of the rushover, is analyzed by means of GLC analysis. The GLC profile is set forth in FIG. 13.

The NMR spectrum for the mixture of geranyl oxyacetaldehyde and neryl oxyacetaldehyde is set forth in FIG. 14.

The infrared spectrum for the mixture of geranyl oxyacetaldehyde and neryl oxyacetaldehyde is set forth in FIG. 15.

EXAMPLE V

Muguet Formulation

The following perfume formulation is prepared:

| Ingredients | Parts by Weight |
|---|---|
| Benzyl acetate | 25 |
| Linalol | 30 |
| Dimethyl benzyl carbinol | 50 |
| Oil of Bergamot | 20 |
| Citronellyl formate | 20 |
| Rhodinol | 150 |
| Heliotropin | 40 |
| Ylang | 10 |
| Cinnamic alcohol | 150 |
| Hydroxy citronellal | 250 |
| Mixture of geranyl oxyacetaldehyde and neryl oxyacetaldehyde prepared according to Example IV | 12 |
| Citronellyl oxyacetaldehyde dimethyl acetal prepared | 8 |

| Ingredients | Parts by Weight |
|---|---|
| according to Example I | 5 |

The addition to the above formulation of the citronellyl oxyacetaldehyde dimethyl acetal prepared according to Example I, and the mixture of geranyl oxyacetaldehyde and neryl oxyacetaldehyde prepared according to Example IV, enhances the muguet note of this muguet formulation.

BRIEF DESCRIPTION OF THE DRAWINGS

FIG. 14 is the NMR spectrum for the mixture of geranyl oxyacetaldehyde and neryl oxyacetaldehyde produced according to Example IV.

FIG. 15 is the infrared spectrum for the mixture of geranyl oxyacetaldehyde and neryl oxyacetaldehyde produced according to Example IV.

Figure 1:
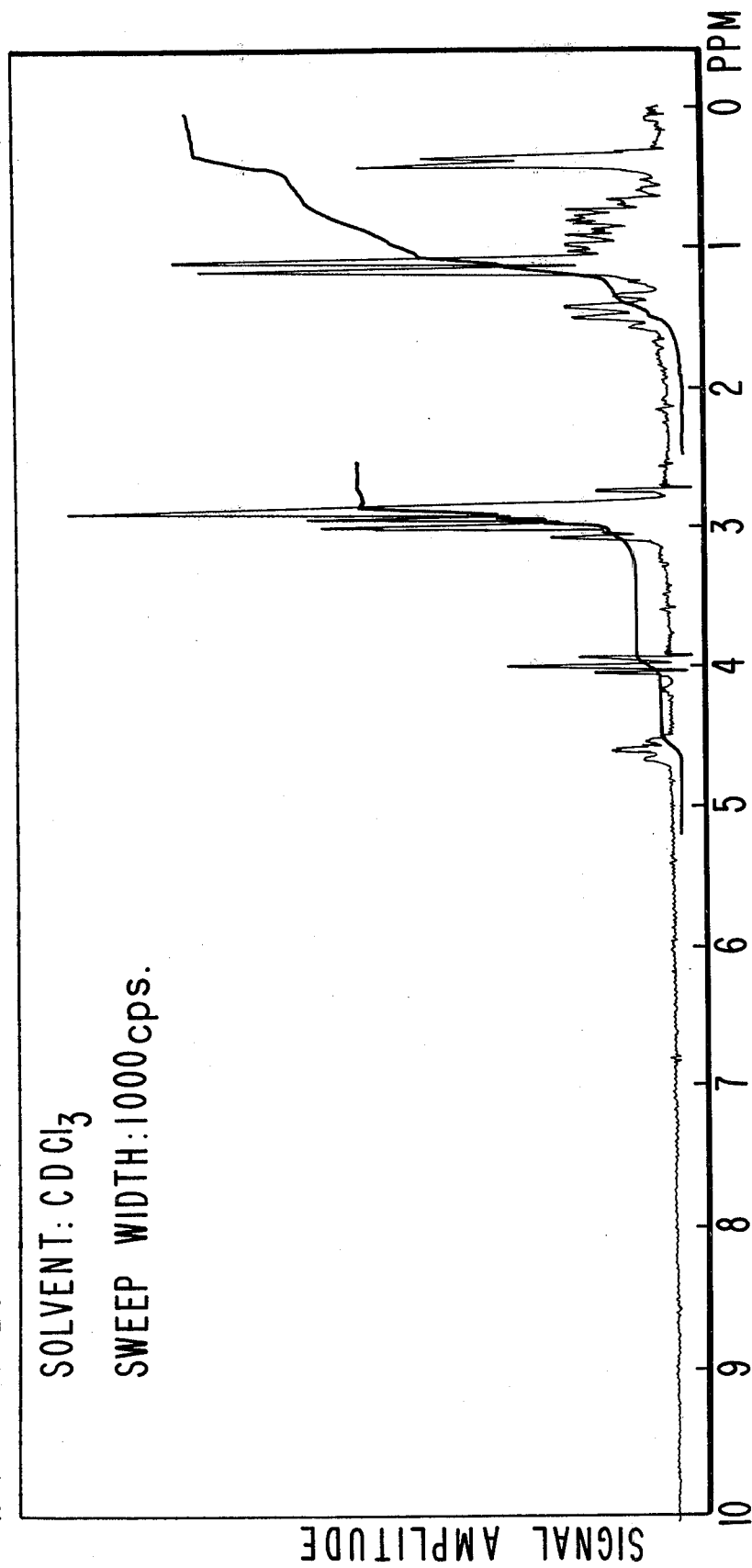
FIG. 1 represents the NMR spectrum for citronellyl oxyacetaldehyde dimethyl acetal prepared according to Example I.
Figure 2:
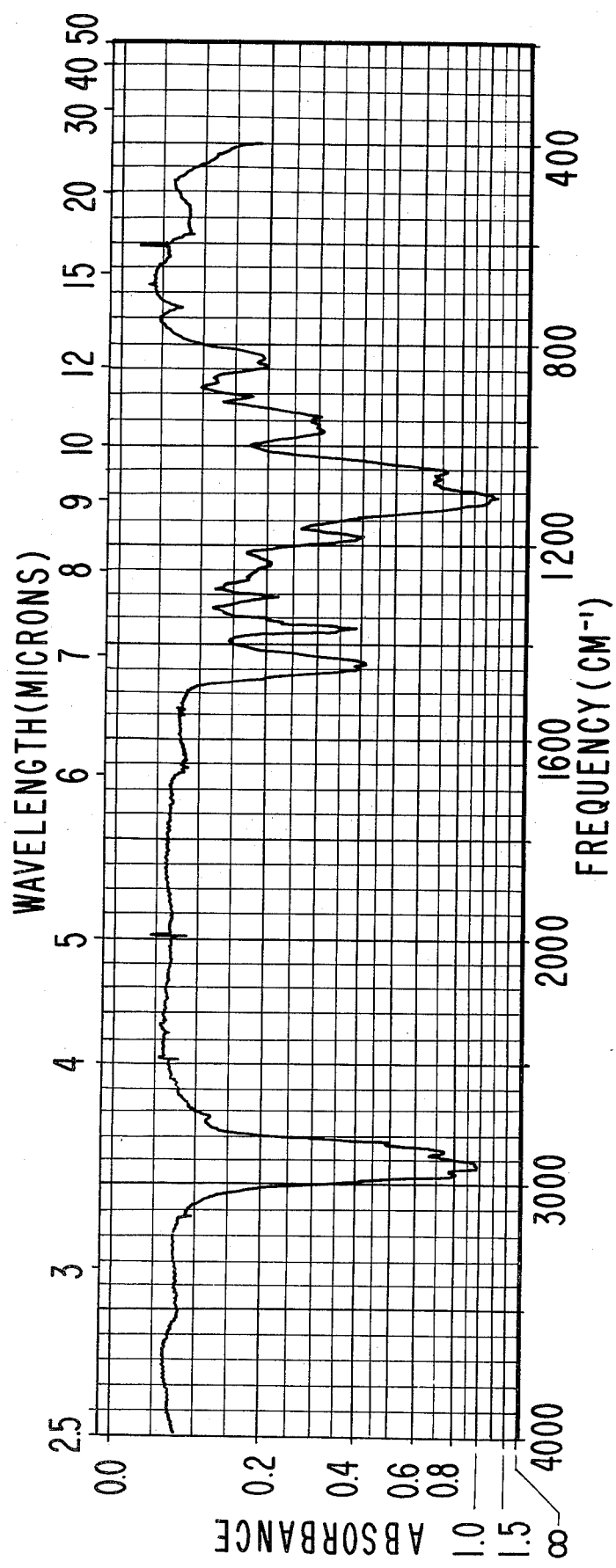
FIG. 2 represents the infrared spectrum for citronellyl oxyacetaldehyde dimethyl acetal prepared according to Example I.
Figure 3:
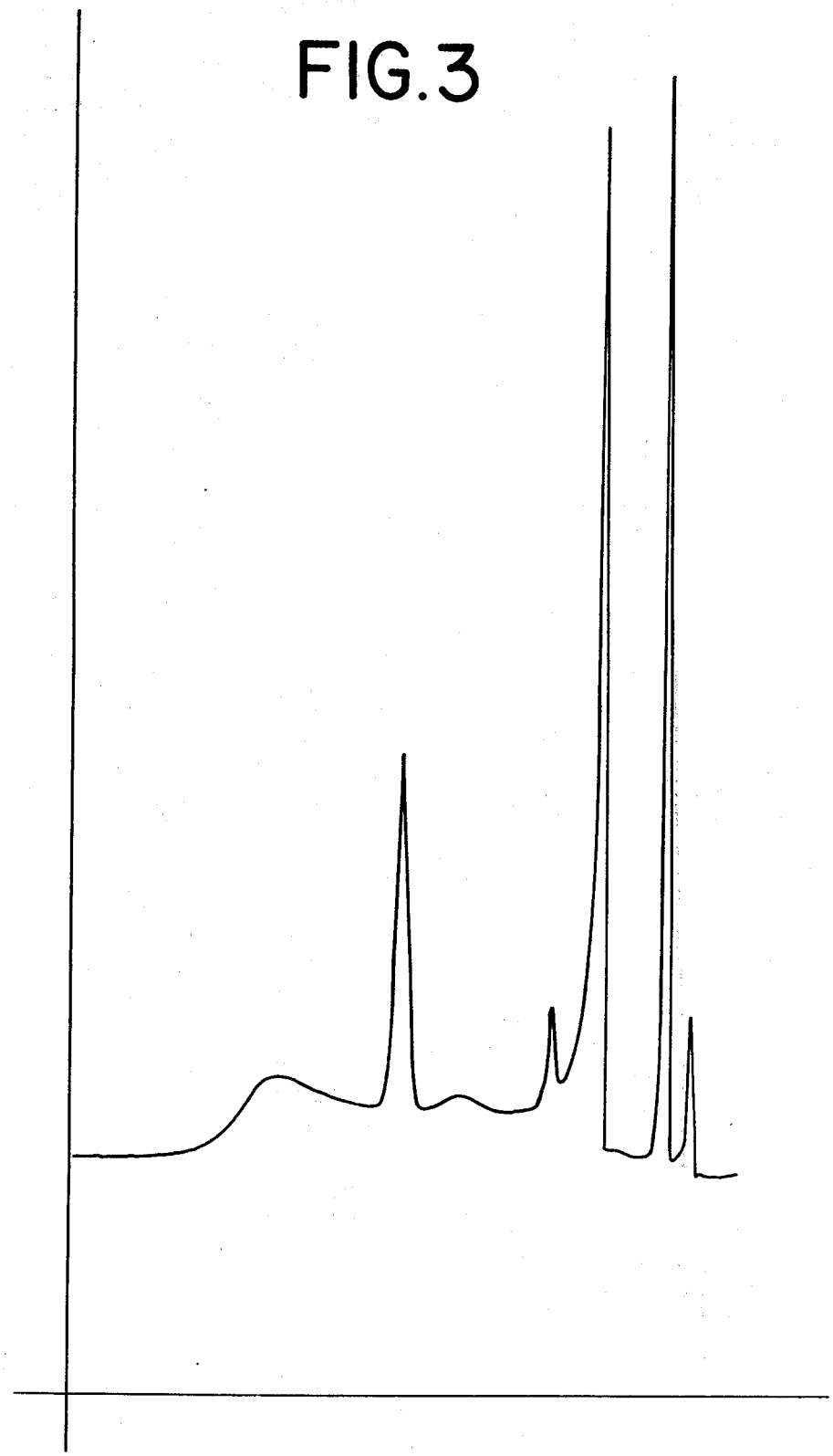
FIG. 3 is the GLC profile for the reaction product of Example II, containing octyl oxyacetaldehyde dimethyl acetal.
Figure 4:
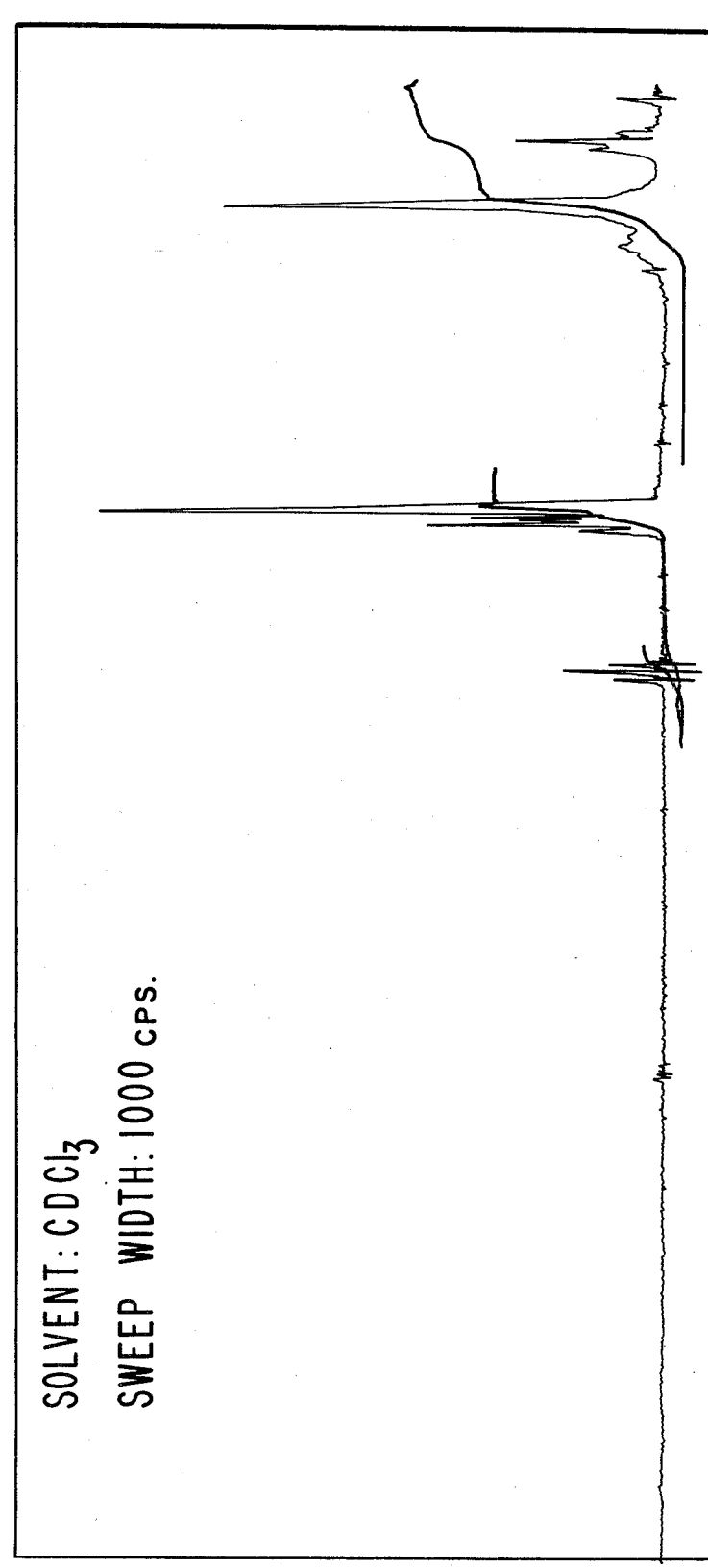
FIG. 4 is the NMR spectrum for octyl oxyacetaldehyde dimethyl acetal produced according to Example II.
Figure 5:
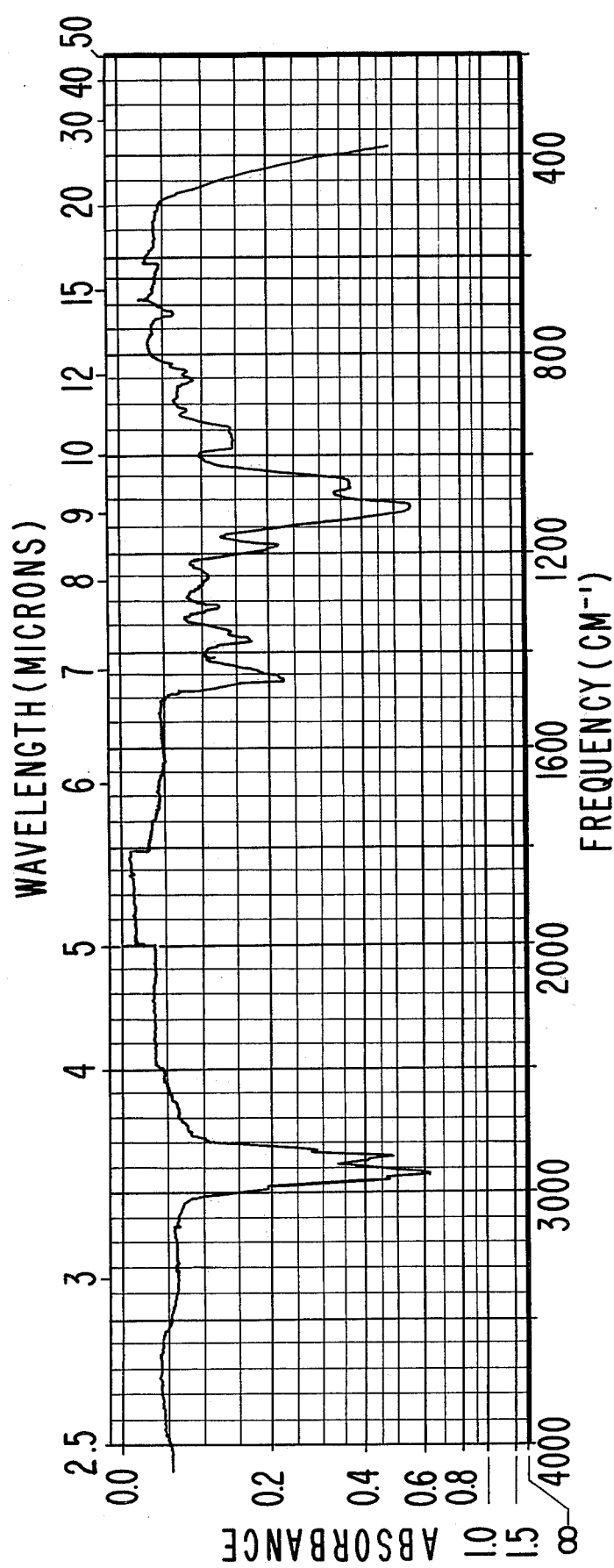
FIG. 5 is the infrared spectrum for octyl oxyacetaldehyde dimethyl acetal produced according to Example II.
Figure 6:
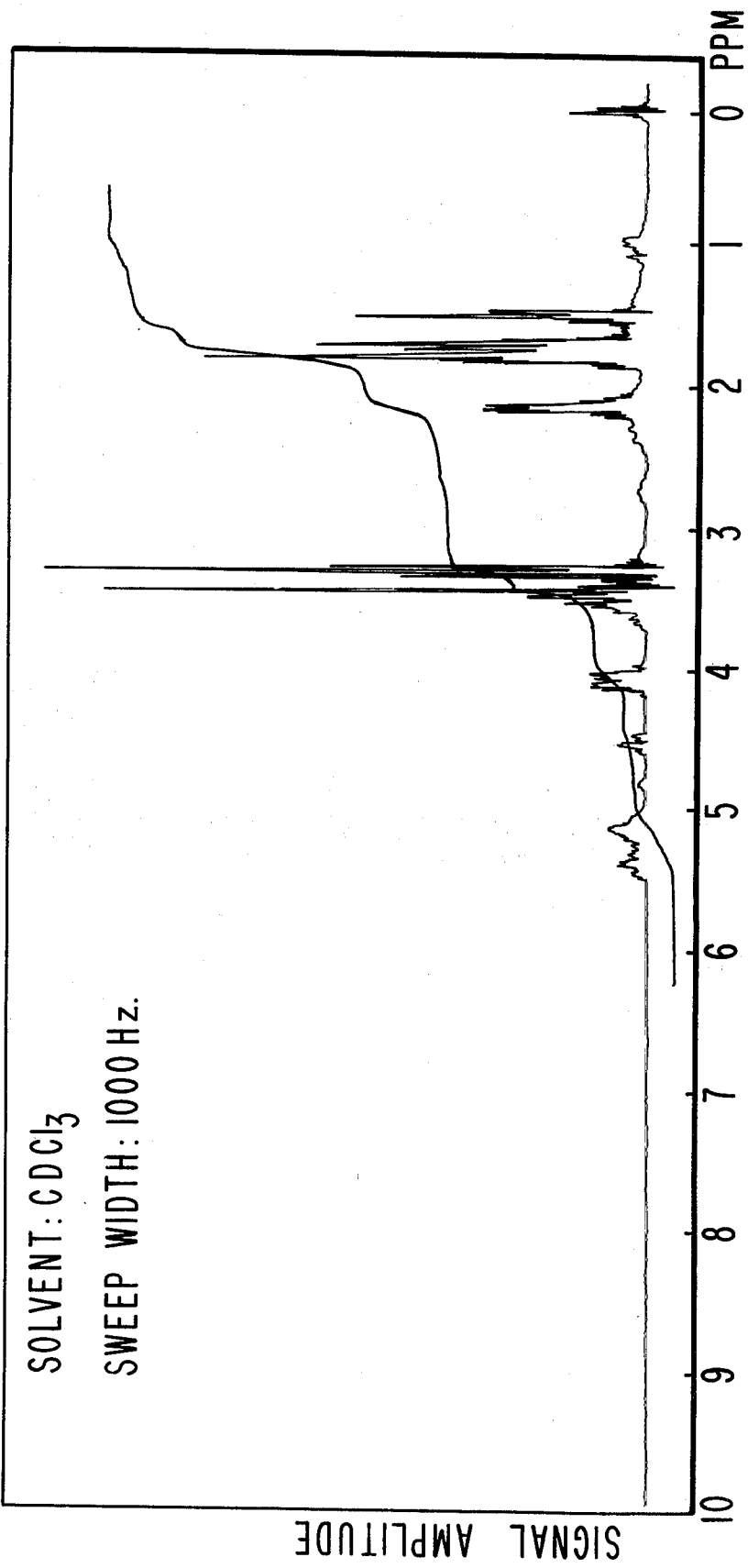
FIG. 6 is the NMR spectrum for the mixture of geranyl oxyacetaldehyde dimethyl acetal and neryl oxyacetaldehyde dimethyl acetal produced according to Example III.
Figure 7:
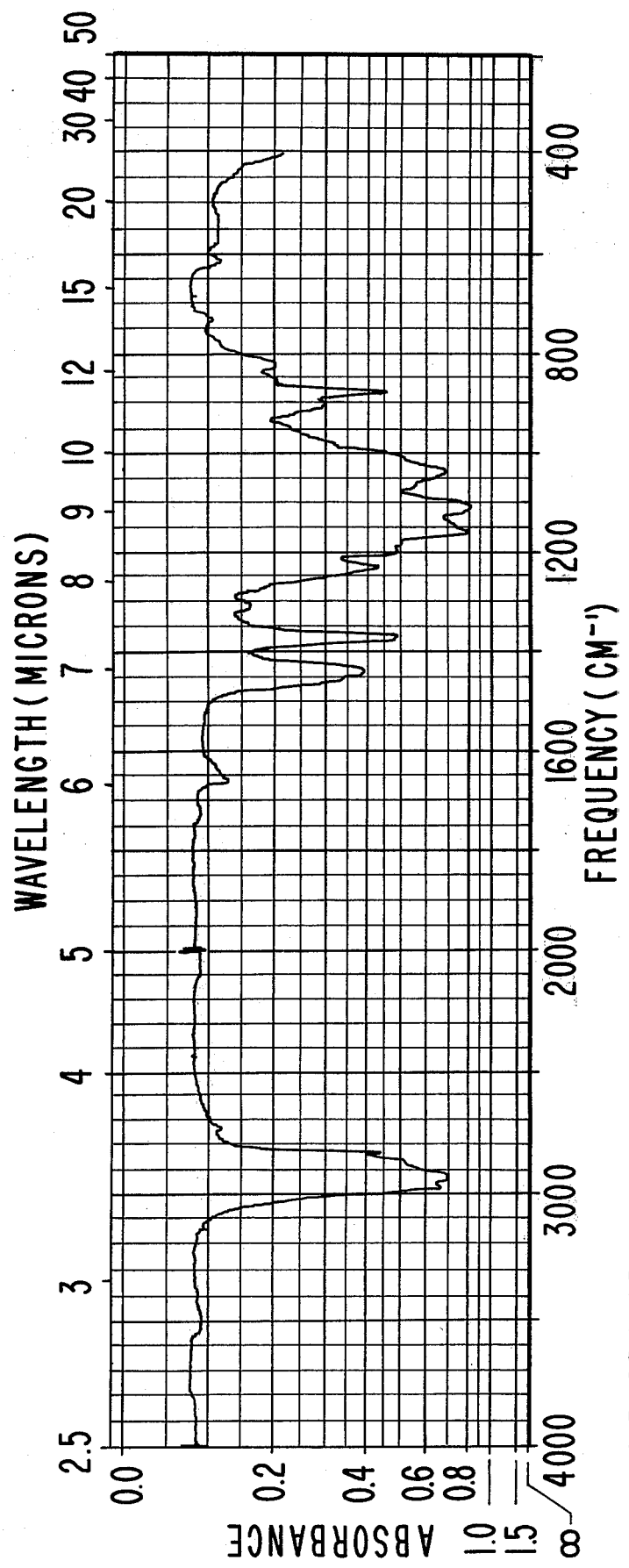
FIG. 7 is the infrared spectrum for the mixture of geranyl oxyacetaldehyde dimethyl acetal and neryl oxyacetaldehyde dimethyl acetal produced according to Example III.
Figure 8:
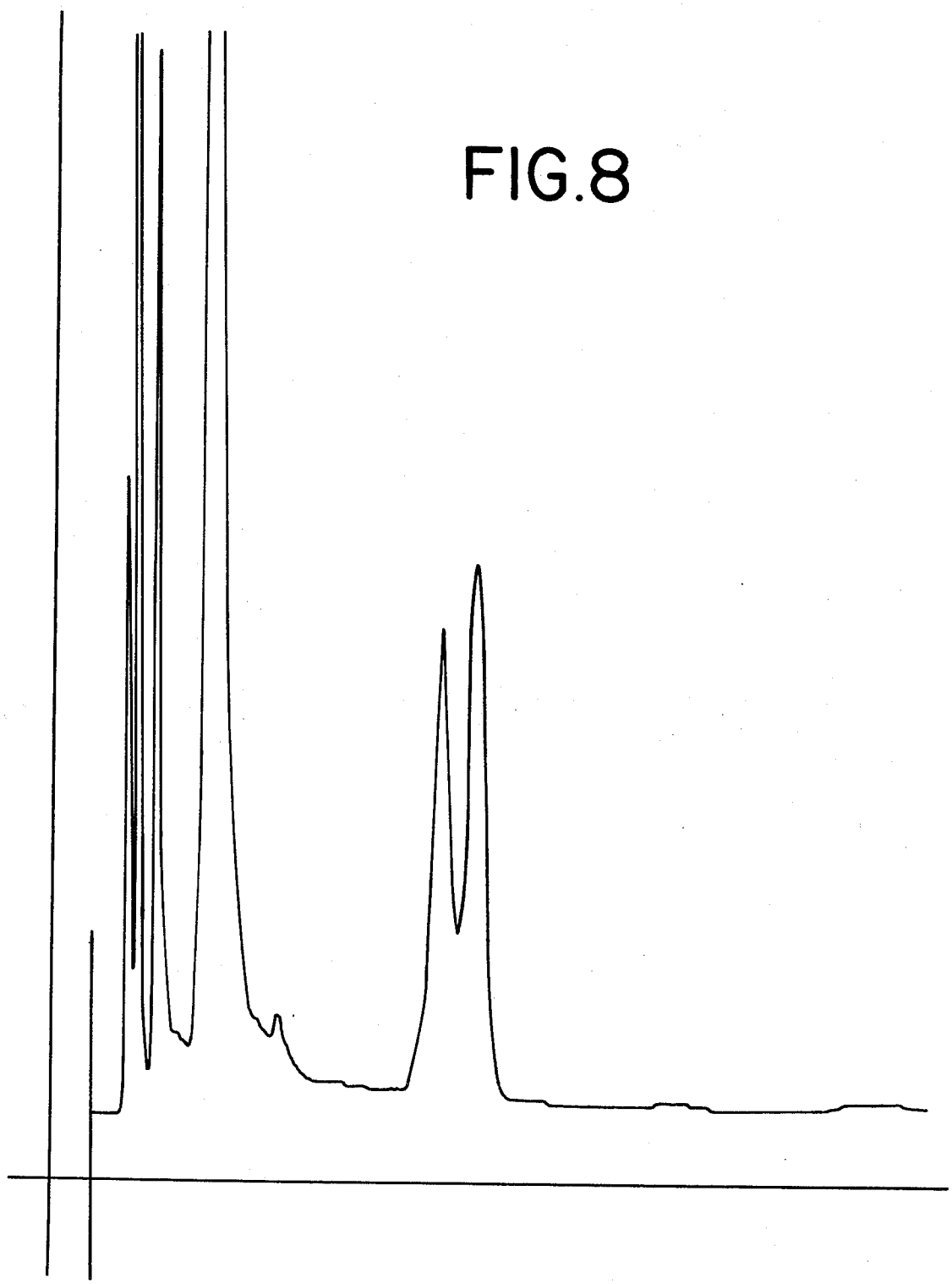
FIG. 8 is the GLC profile for the reaction product containing the mixture of geranyl oxyacetaldehyde dimethyl acetal and neryl oxyacetaldehyde dimethyl acetal produced according to Example III.
Figure 9:
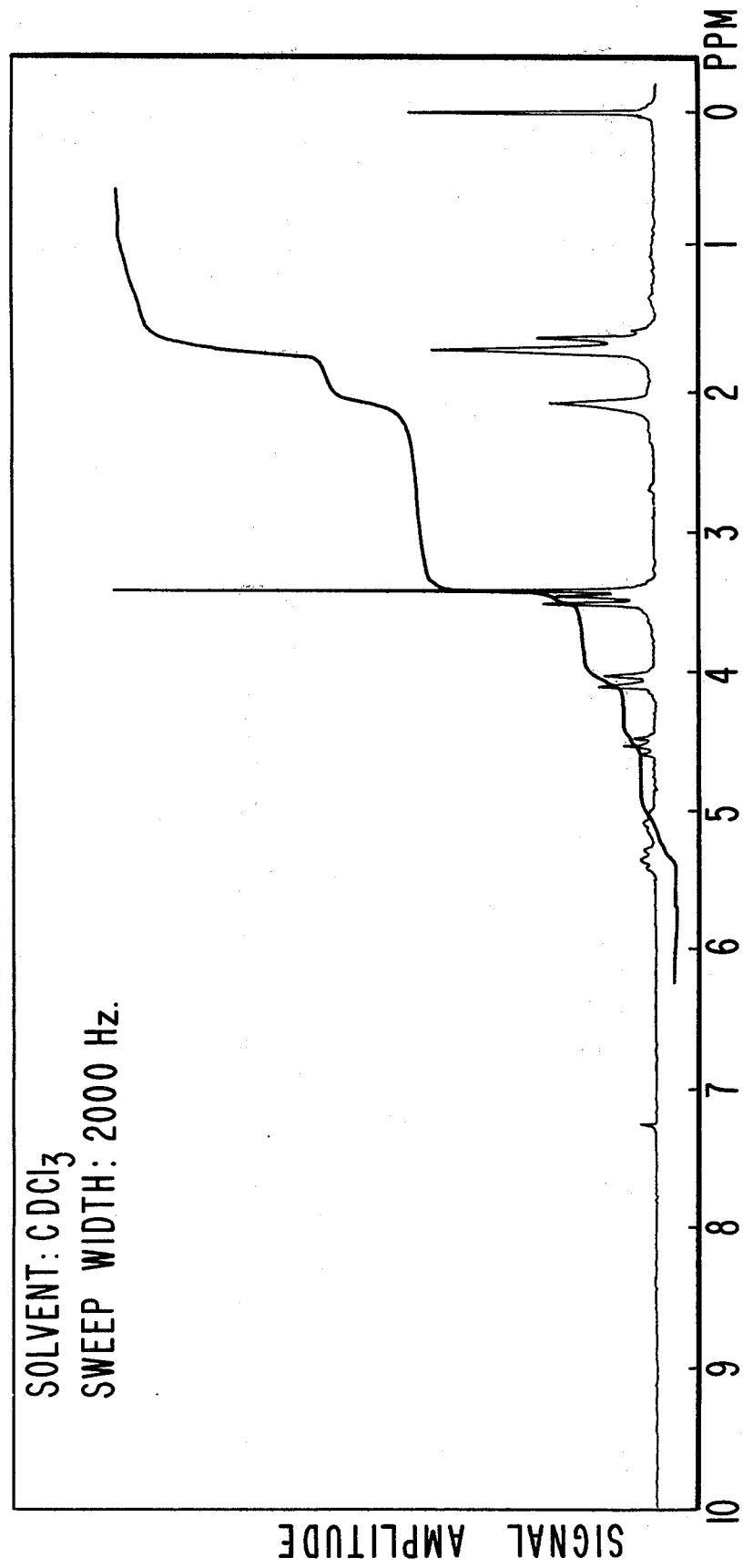
FIG. 9 is the NMR spectrum for geranyl oxyacetaldehyde dimethyl acetal produced according to Example III.
Figure 10:
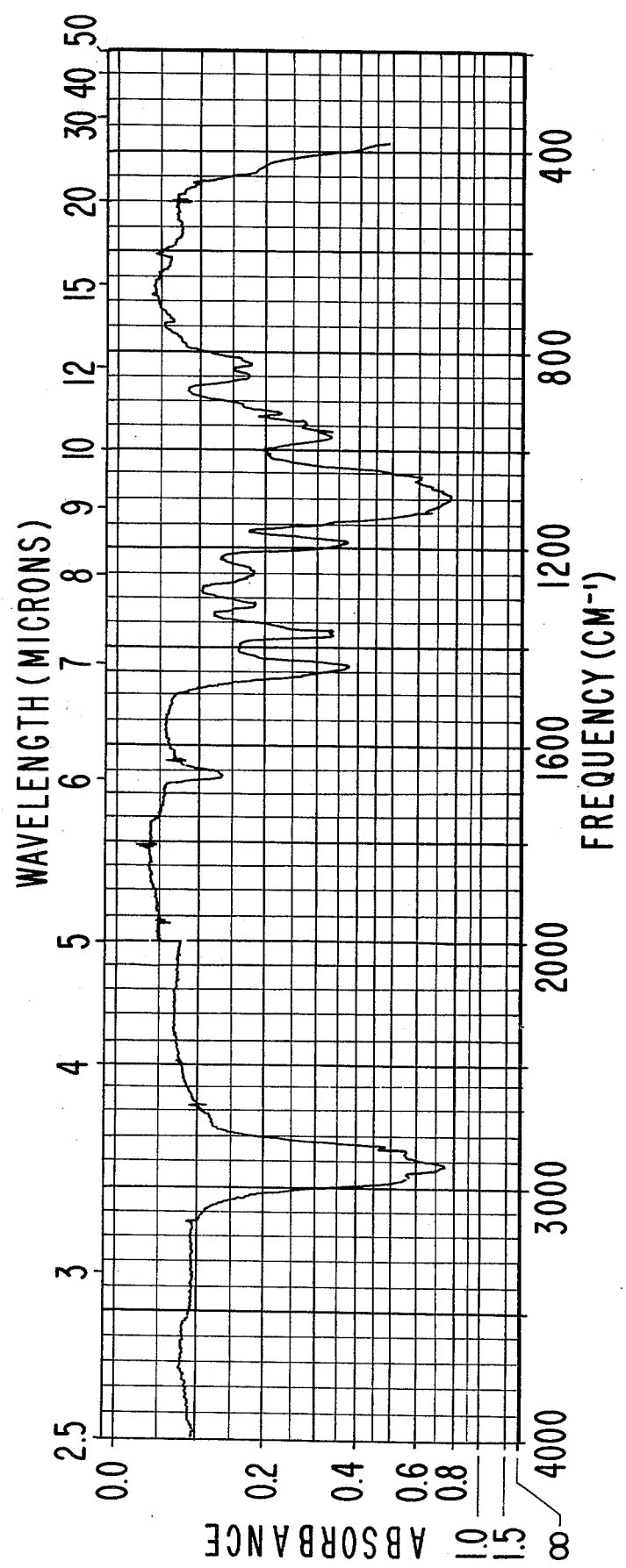
FIG. 10 is the infrared spectrum for geranyl oxyacetaldehyde dimethyl acetal produced according to Example III.
Figure 11:
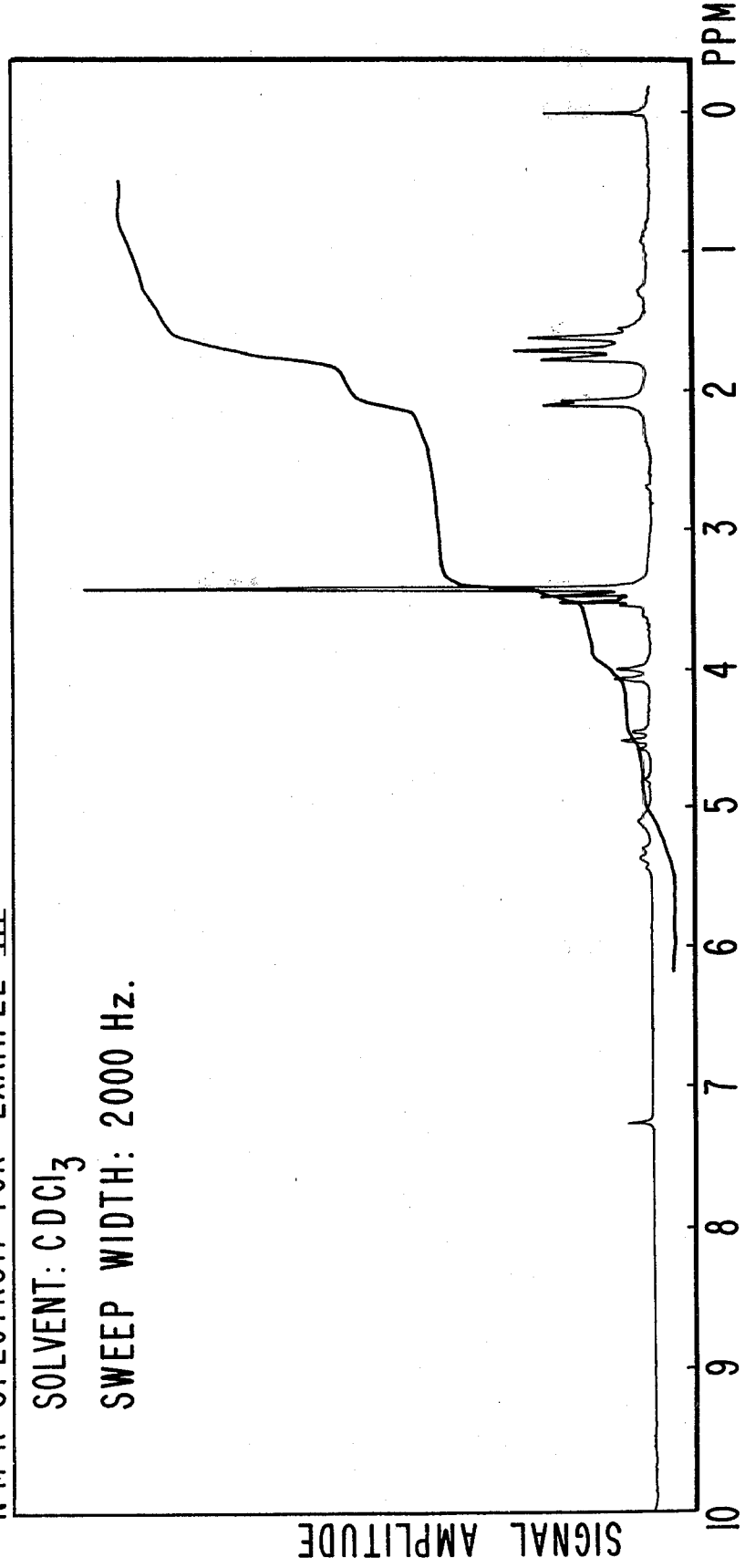
FIG. 11 is the NMR spectrum for neryl oxyacetaldehyde dimethyl acetal produced according to Example III.
Figure 12:
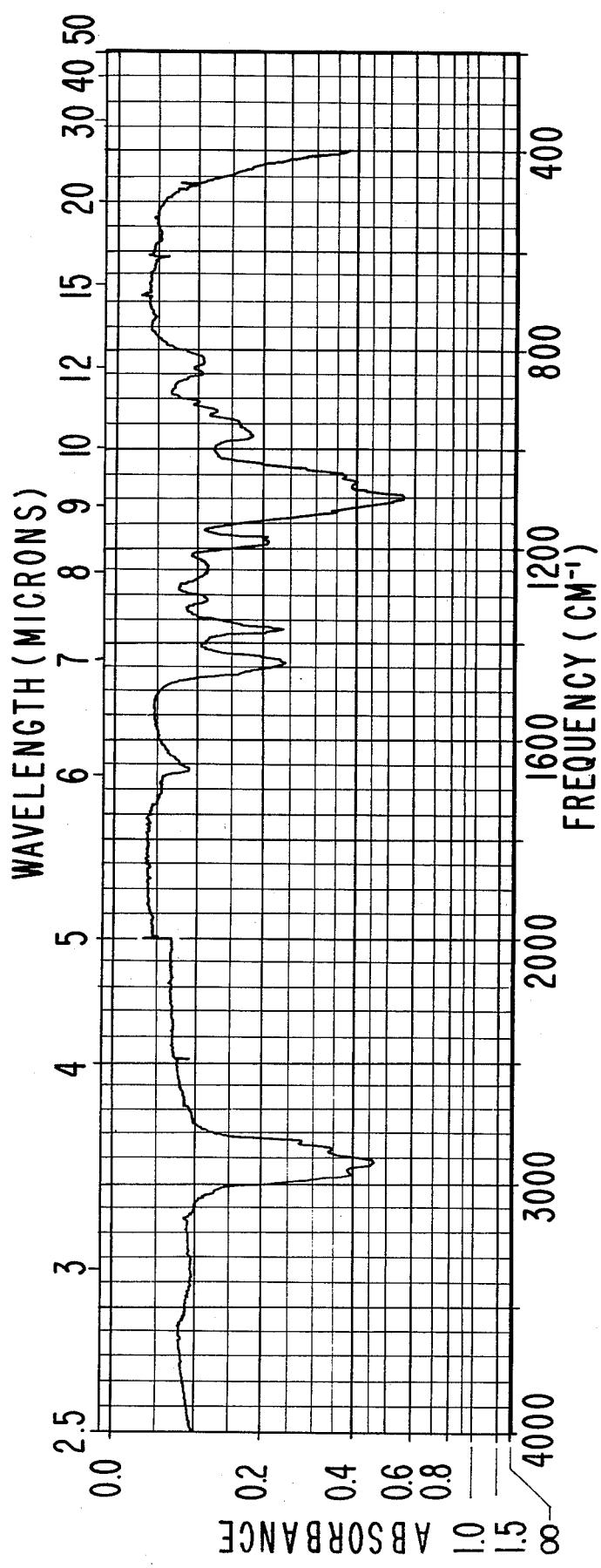
FIG. 12 is the infrared spectrum for neryl oxyacetaldehyde dimethyl acetal produced according to Example III.
Figure 13:
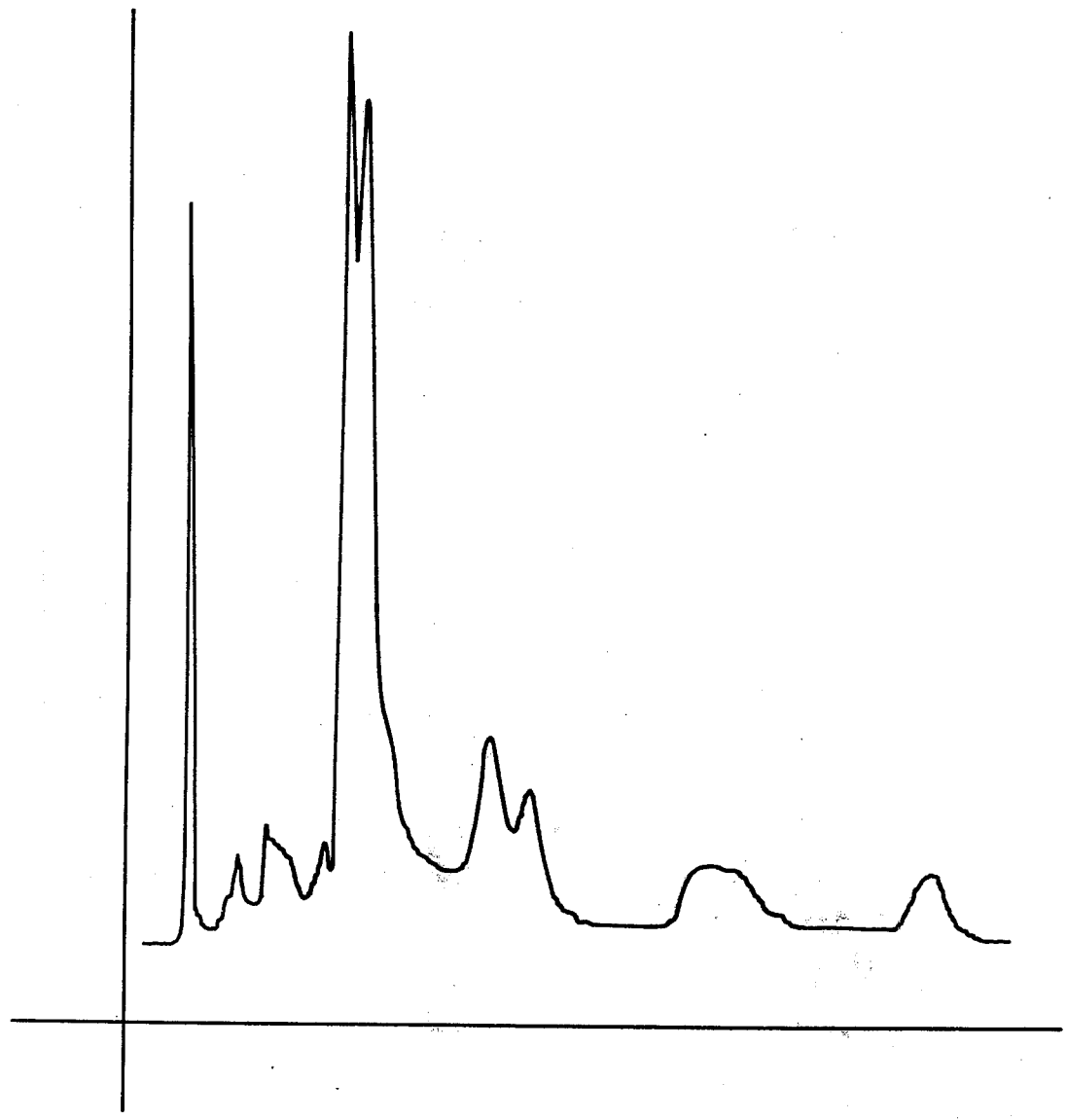
FIG. 13 is the GLC profile for the reaction product of Example IV containing a mixture of geranyl oxyacetaldehyde and neryl oxyacetaldehyde.

What is claimed is:

1. A process for producing a mixture of geranyl oxyacetaldehyde dimethyl acetal and neryl oxyacetaldehyde dimethyl acetal according to the reaction:

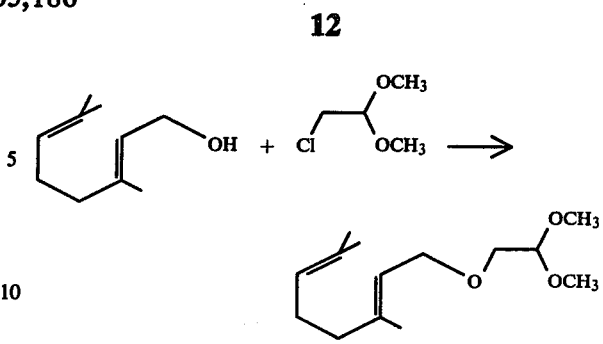

comprising the step of intimately admixing a mixture of geraniol and nerol with chloroacetaldehyde dimethyl acetal in the presence of a base selected from the group consisting of sodium hydroxide and potassium hydroxide and a phase transfer agent which is tricapryl methyl ammonium chloride; the reaction temperature being in the range of from 120° C. up to about 200° C.; the mole ratio of the mixture of geraniol and nerol to chloroacetaldehyde dimethyl acetal being between 0.5:1 up to 2:1; the mole ratio of mixture of geraniol and nerol to base being from 1:1 up to 1:2, the concentration or tricapryl methyl ammonium chloride in the reaction mass based on amount of chloroacetaldehyde dimethyl acetal being in the range of from 0.5 grams of tricapryl methyl ammonium chloride per mole of chloroacetaldehyde dimethyl acetal up to 25 grams of tricapryl methyl ammonium chloride per mole of chloroacetaldehyde dimethyl acetal; the reaction being carried out in the absence of solvent of in the presence of a solvent selected from the group consisting of xylene and decalin; then fractionally distilling the resulting product whereby the mixture of geranyl oxyacetaldehyde dimethyl acetal and neryl oxyacetaldehyde dimethyl acetal is recovered.

2. A process for the preparation of citronellyloxyacetaldehyde dimethyl acetal according to the reaction:

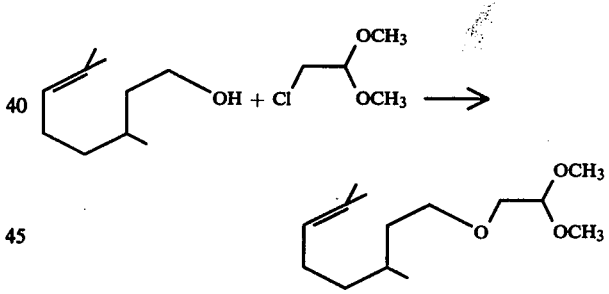

comprising the step of intimately admixing citronellol with chloroacetaldehyde dimethyl acetal in the presence of a base selected from the group consisting of sodium hydroxide and potassium hydroxide and a phase transfer agent which is tricapryl methyl ammonium chloride, the reaction temperature being in the range of from 120° C. up to about 200° C.; the mole ratio of citronellol to chloroacetaldehyde dimethyl acetal being between 0.5:1 and 2:1; the mole ratio of citronellol to base being from 1:1 up to 1:2; the concentration of tricapryl methyl ammonium chloride in the reaction mass base on amount of chloroacetaldehyde dimethyl acetal being in the range from 0.5 grams of tricapryl methyl ammonium chloride per mole of chloroacetaldehyde dimethyl acetal up to 25 grams of tricapryl methyl ammonium chloride per mole of chloroacetaldehyde dimethyl acetal; the reaction being carried out in the presence of solvent or in the presence of a solvent selected from the group consisting of xylene, and decalin; then fractionally distilling the resulting product whereby citronellyloxyacetaldehyde dimethyl acetal is recovered.

* * * * *